US011871863B2

(12) United States Patent
Kim

(10) Patent No.: US 11,871,863 B2
(45) Date of Patent: Jan. 16, 2024

(54) HEIGHT-ADJUSTABLE PILLOW

(71) Applicant: Joung Gug Kim, Gyeonggi-do (KR)

(72) Inventor: Joung Gug Kim, Gyeonggi-do (KR)

( * ) Notice: Subject to any disclaimer, the term of this patent is extended or adjusted under 35 U.S.C. 154(b) by 535 days.

(21) Appl. No.: 17/264,894

(22) PCT Filed: Aug. 1, 2019

(86) PCT No.: PCT/KR2019/009616
§ 371 (c)(1),
(2) Date: Feb. 1, 2021

(87) PCT Pub. No.: WO2020/027603
PCT Pub. Date: Feb. 6, 2020

(65) Prior Publication Data
US 2021/0298499 A1   Sep. 30, 2021

(30) Foreign Application Priority Data

Aug. 3, 2018  (KR) .......................... 10-2018-0090609

(51) Int. Cl.
*A47G 9/10* (2006.01)
(52) U.S. Cl.
CPC .... *A47G 9/1036* (2013.01); *A47G 2009/1018* (2013.01)
(58) Field of Classification Search
CPC .................. A47G 9/1036; A47G 9/10; A47G 2009/1018; A47G 9/109
See application file for complete search history.

(56) References Cited

U.S. PATENT DOCUMENTS

| 3,243,828 | A | * | 4/1966 | McCarty | .................. A47G 9/10 |
| | | | | | 5/636 |
| 5,781,947 | A | * | 7/1998 | Sramek | .................. A47G 9/109 |
| | | | | | 5/636 |
| 6,671,906 | B1 | * | 1/2004 | Milligan | ................ A47G 9/109 |
| | | | | | 5/636 |

FOREIGN PATENT DOCUMENTS

| KR | 2020110011322 | 12/2011 |
| KR | 200474522 | 2/2014 |
| KR | 20140130885 | 11/2014 |

* cited by examiner

*Primary Examiner* — Fredrick C Conley
(74) *Attorney, Agent, or Firm* — IPLA P.A.

(57) ABSTRACT

A height-adjustable pillow includes: a cervical pillow including an outer shell and contents filled inside the outer shell, and wall parts formed to protrude from both sides of the loading part; side pillows including side-of-face contact parts, which are attached to both sides of the cervical pillow and have a plurality of elastic pads formed in the same shape and stacked therein, and fine height-adjusting parts comprising a plurality of slim pads stacked at the lower portions of the side-of-face contact parts and cover bodies which are finished by respectively encompassing the outer surfaces of the plurality of slim pads and being thermally fused to the edge portions thereof and which have friction increasing parts provided on the outer surfaces thereof; wing parts for connecting the lower portions of the cervical pillow and the side pillows; and an outer cover in which all constituent parts are accommodated and fitted.

8 Claims, 5 Drawing Sheets

HEIGHT-ADJUSTABLE PILLOW

BACKGROUND

The present invention relates to a height-adjustable pillow, and more particularly, to a height-adjustable pillow, which has excellent air permeability and can adjust its height according to a user's weight and shoulder level.

In general, a pillow supports the back of the head, namely, a user's occipital region. Because the user's head is bent down when the occipital region is supported, the C-shaped cervical vertebrae are pressed to be bent inversely, and the muscles at the back of the neck get stiff.

Therefore, the user does not feel refreshed and feels stiff in the neck even though taking sleep. If the condition persists, it may cause diseases, such as a cervical disk or neck pains.

In order to overcome the above-mentioned problem, Korean Patent Publication No. 10-2014-0130885 discloses a cervical pillow, Korean Utility Model Registration No. 20-0471522 discloses a pillow for supporting cervical vertebrae and thoracic vertebrae, and Korean Utility Model Registration No. 20-0458054 discloses a pillow for correcting cervical vertebrae. All of the conventional arts have the structure to keep a user's head low to support the neck region so as to simply maintain the cervical vertebrae.

However, because the pillows according to the conventional arts simply and slightly support the user's cervical vertebrae in a state where the user lies on his or her back, if the user's head moves on the pillow in his or her sleep, the user feels stiff in the neck after sleep.

Moreover, when the user rolls over on his or her side in sleep using one of the vertebral pillows, because the ears, the temporomandibular joint, and the optic nerve are pressed by weight of the head, the user feels great inconvenience. Especially, the ears with relatively lower intensity are pressed to be stuck to the temporal region, and it may cause an earache and the user feels stuffy. Furthermore, a mastoid which is located at the back of the ear is a part of the skull with great intensity is pressed by the pillow, and it may cause a headache.

It is no exaggeration to say that such problems are caused since the pillows cannot cope with a change in the user's body type and weight.

SUMMARY OF THE INVENTION

Accordingly, the present invention has been made in an effort to solve the above-mentioned problems occurring in the prior arts, and it is an object of the present invention to provide a height-adjustable pillow, which can relax the fasciae and stimulate blood circulation by pressurizing articulated sections between the cervical vertebrae and the occipital bones, prevent the ears, the temporomandibular joint, and the optic nerve from being pressed by weight of the head when a user rolls over on his or her side in sleep, make the shoulders comfortable in sleep without being caught to the pillow, prevent the pillow from being separated from the user's head, allow the user to sleep with his or her head on the pillow in a cool condition through ventilation and cooling actions, and provide a repulsive elasticity due to a cushiony action by through holes.

It is another object of the present invention to provide a height-adjustable pillow, which includes a minute height-adjusting part to adjust height between the face and the shoulders when the user rolls over on his or her side.

To achieve the above objects, the present invention provides a height-adjustable pillow including: a cervical pillow including an outer shell and contents filled inside the outer shell so as to provide elasticity, wherein the outer shell and the contents have a loading part, which is recessed such that the cervical vertebrae and the occipital vertebrae are put thereon, and wall parts formed to protrude from both sides of the loading part; side pillows including side-of-face contact parts, which are attached to both sides of the cervical pillow and have a plurality of elastic pads formed in the same shape and stacked therein, and fine height-adjusting parts including a plurality of slim pads stacked at the lower portions of the side-of-face contact parts and cover bodies which encompass the outer surfaces of the plurality of slim pads and are formed by thermosetting to the edges thereof and which have friction increasing parts provided on the outer surfaces thereof; wing parts for connecting the lower portions of the cervical pillow and the side pillows;

and an outer cover in which all constituent parts are accommodated and fitted.

The slim pads of the fine height-adjusting parts are 4.5 to 5.5 mm in thickness.

The friction increasing parts are made with any one among lylex, suede, velvet and woven fabric.

Moreover, the elastic pads and the slim pads have the same shape and form when viewed from the top.

Furthermore, the elastic pads and the slim pads are made of polyethylene foam, polyurethane foam, or EVA foam. The side-of-face contact parts have ear seating parts and ventilation holes.

Additionally, the side-of-face contact parts have first sponges of a filter foam material and second to fourth sponges of a highly elastic polyurethane foam material or a memory foam material, which are stacked alternately.

In addition, the cervical pillow and the side-of-face contact parts have cooling pads with a plurality of pieces of urethane gel stacked therein, and the cervical pillow has a plurality of acupressure protrusions formed to protrude.

When people use the height-adjustable pillow of a 3D type, which has repulsive elasticity by a special cushiony action of PU FOAM in which various materials are mixed, the following effects are obtained.

First, since the height-adjustable pillow is a cervical pillow of a neck-fixing type differently from conventional pillows, it can change a turtle neck or a forward neck into a C-shaped neck. The M-shaped pillow can fix the neck and the head to prevent the cervical vertebrae from being bent or separated, and pressurize the articulated sections between the cervical vertebrae and the occipital bones so as to relax the fasciae and stimulate blood circulation.

Second, the ¬-shaped grooves prevents the ears, the temporomandibular joint, and the optic nerve from being pressed by weight of the head since inducing the ears, the temporomandibular joint, and the optic nerve to be put in the spaces of the grooves when the user rolls over on his or her side in sleep.

Third, the recess parts of the side pillows prevent the user's shoulders from being caught to the pillows in sleep, and the wing parts prevent the pillow from being separated from the head, so that the user can take a sound sleep comfortably.

Fourth, the right and left side pillows have layers of the sponges of various kinds stacked therein and ventilation holes to provide excellent elasticity, provide a ventilation effect using filter foams, and allows the user to sleep on the pillow in a cool condition using a plurality of pieces of urethane gel or condensed charcoal serving as refrigerant.

Fifth, if the user folds the cervical pillow and the side pillows, the user can watch TV or read books comfortably.

Sixth, because the height-adjustable pillow makes the user's face and shoulders at a right angle when rolling over on his or her side, the cervical vertebrae and the backbones keep in a straight line, and the user can sleep comfortably even when rolling over on his or her side.

DETAILED DESCRIPTION OF THE INVENTION

Figure 8:
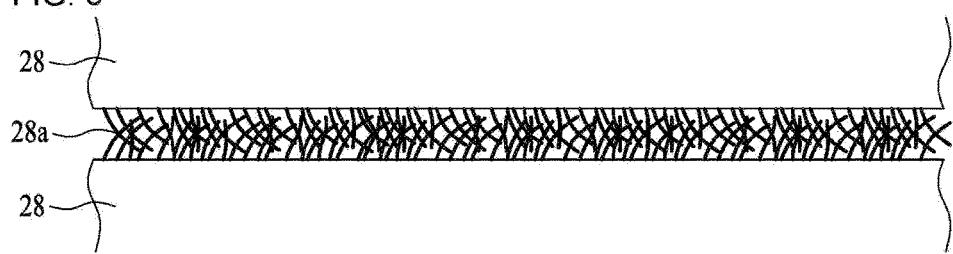
FIG. 8 is a partially enlarged view of a stacked portion of the side pillow of the height-adjustable pillow according to the preferred embodiment of the present invention.

FIG. 8 is a partially enlarged view of a stacked portion of a side pillow of a height-adjustable pillow according to a preferred embodiment of the present invention.

As shown in the drawing, the height-adjustable pillow 100 according to the preferred embodiment of the present invention includes a cervical pillow 10, side pillows 20 disposed at both sides of the cervical pillow 10, wing parts 30 for connecting the cervical pillow 10 with the side pillows 20, and an outer cover 60 for covering all of the components.

An outer shell 11 is made of polyethylene foam (PE FOAM) or ethylene vinyl acetate foam (EVA FOAM) in order to provide an acupressure effect. Contents 12 of the outer shell 11 are made of polyurethane foam to provide a cushiony sense when a user uses the pillow. Therefore, the height-adjustable pillow according to the preferred embodiment of the present invention provides an appropriate elasticity differently from the conventional pillows due to stiffness of the outer shell 11 and a highly elastic sponge function of the contents 12. So, the height-adjustable pillow according to the preferred embodiment of the present invention can provide a function differentiated from the conventional pillows in that the height-adjustable pillow is not stiff and is not sunken suddenly.

The cervical pillow 10 includes a loading part 13 recessed so that the cervical vertebrae and the occipital bones are put on the loading part 13, and an M-shaped wall part 14 protruding upwards from both sides of the loading part 13 to support both sides of the user's head. The loading part 13 is formed in a shape of C.

Moreover, the cervical pillow 10 has a wide head part and a narrow neck part to support the user's head from a start point of the neck bone without touching the shoulder wings, so that the user can feel comfortable when lying back.

Figure 2:
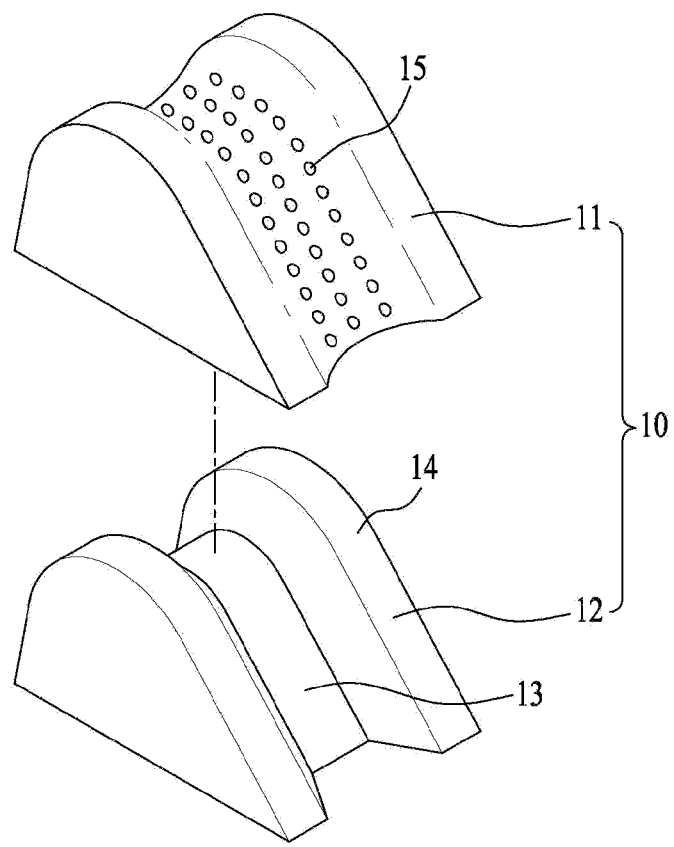
FIG. 2 is an exploded perspective view of a cervical pillow of the height-adjustable pillow according to the preferred embodiment of the present invention.

Furthermore, as shown in FIG. 2, the cervical pillow 10 has an acupressure protrusion 15 disposed on an upper portion of the cervical pillow 10 so as to provide an acupressure effect when the user lies down with his or her head on the pillow.

Here, the outer shell 11 of the cervical pillow 10 is made in such a way that the C-shaped loading part 13 and the M-shaped wall part 14 for fixing the head and the neck are formed of PE foam and EVA foam in a mold in order to pressurize the articulated sections between the cervical vertebrae and the occipital bones. The contents 12 which fill inside the outer shell 11 to provide elasticity are made of polyurethane foam or memory foam with high elasticity. A lower portion of the outer shell 11 is finished to be perfectly sealed with polyethylene foam or EVA foam by thermosetting bonding so that the contents 12 are not separated.

Additionally, in order to stabilize and fix the molded cervical pillow and adjust the height of the cervical pillow, it is also possible that the lowermost part of the cervical pillow has two or three layers made of highly elastic polyurethane foam or memory foam in constant thickness.

Figure 3:
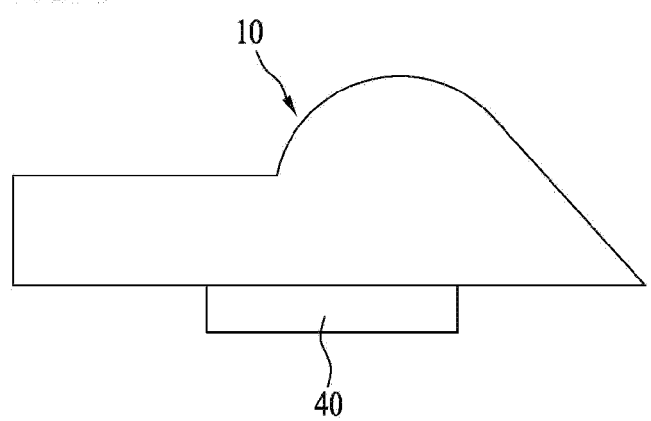
FIG. 3 is a side sectional view showing a state where a floor support part disposed at the bottom of the cervical pillow of the height-adjustable pillow according to the preferred embodiment of the present invention.

As shown in FIG. 3, a floor support part 40 is disposed at the C-shaped lower portion of the cervical pillow 10 to form a lever shape so that a heavy part is naturally put on the floor.

That is, when the floor support part 40 of a short pad is adhered on the bottom of the C-shaped cervical portion of the cervical pillow 10 to form a seesaw-like shape, the upper portion to support the head from the neck down is seated comfortably and naturally toward the heavy part due to a space from the floor.

The side pillow 20 includes: an ear seating part 23 to prevent the ear from being pressed when the user lies on his or her side; and ventilation holes 24 to be ventilated well. The side pillows 20 are attached to both sides of the cervical pillow 10.

The side pillow 20 includes a side-of-face contact part 26, and fine height-adjusting parts 29 stacked below the side-of-face contact part 26.

The side-of-face contact part 26 is not a united part, differently from the conventional pillows, but is an elastic pad separately formed. The side-of-face contact part 26 includes a first sponge 21 made of filter foam and second to fourth sponges 22 made of polyurethane material in consideration of ventilation and elasticity. The first sponge 21 and the second to fourth sponges 22 are stacked alternately (here, the materials are memory foam and filter foam with high elasticity and density of 3-25 kg/m, 35 kg/m, 40 kg/m, or others).

The side-of-face contact part 26 has the first sponge 21 and the second to fourth sponges 22 stacked alternately and the ventilation holes 24 so as to provide ventilation effect and quickly repulsive elasticity.

The side-of-face contact part 26 has a recess part 25 formed inwardly so that the user's shoulder is put on the upper portion of the wing part 30 without being caught to the side pillow 20 when the user lies on his or her side.

Therefore, the user's head can be put on the pillow comfortably without being caught to the pillow while sleeping.

Like the conventional functional pillows, the ear seating part 23 has a hole shape so that the ears are not pressed when the user lies on his or her side or has a concave shape so that the user's face does not roll in sleep. In the present invention, the ear seating part 23 is inclined with the width of 20 to 30 mm or is formed in a bar shape with the width of 20 to 30 mm, and has a sponge attached to a middle layer of the pillow or to the edge of a lower end portion of the pillow so as to be concave. The "¬"-shaped ear portion has the form of a baseball helmet to protect from the head to the chin so as to make the chins, the ears, and the optic nerves of the eyes comfortable. The sponge for the ear seating part 23 is softer than the sponges of other parts so that the ears, the temporomandibular joint, or the optic nerves are not pressed by the weight of the head.

Moreover, the side-of-face contact part 26 has a plurality of cooling pads 50 of urethane gel or a plurality of pieces of compressed charcoals. The cooling pads 50 are made of cooling gel or a phase changing material to absorb the user's temperature in sleep.

In case that the cooling pads 50 are made of urethane gel, the lower portion of the side pillow 20 made with a urethane film is molded to be round and hollow, and then, liquid urethane gel is poured and solidified in the loading part.

That is, since the liquid urethane gel is put and solidified in the loading part of the cervical pillow 10 covered with the urethane film, the loading part has cooling and acupressure effect.

If a cooling pad 50 of a face size which is made of urethane gel is put on the pillow, it is inconvenient for use due to stiffness of the cooling material. On the contrary, if a plurality of the cooling pads 50 of a small size are adhered on the pillow, the cooling pads may fulfill their function as cooling pads according to the form of the face.

The fine height-adjusting parts 29 are formed below the side-of-face contact part 26 to minutely adjust the height according to the width of the shoulders and the size of the face so as to keep a right angle between the face side and the shoulders.

Each of the fine height-adjusting part 29 includes a plurality of slim pads 27 and a cover body 28. Viewed from the top, the slim pads 27 have the same shape and form as the elastic pads.

Furthermore, the slim pads 27 are made of the same material as the side-of-face contact part 26, such as polyethylene foam, polyurethane foam or EVA foam.

In this instance, if shoulder muscles are decreased or increased due to a change in weight of the user, the slim pads 27 can change the angle between the shoulders and the side of the face when the side of the face gets in close contact with the side-of-face contact part 26.

That is, a user who works out his or her muscles a lot has developed shoulder muscles and wide shoulders. When such a user lies on his or her side and makes his or her face get in close contact with the side-of-face contact part 26, the side of the face is inclined downwards from a position higher than the side-of-face contact part 26 and gets in close contact with the side-of-face contact part.

On the contrary, if the user loses weight in the face or the shoulders suddenly, when the user lies on his or her side, the angle between the face and the shoulders gets higher than a right angle, so that the shoulders and the neck cannot keep perpendicular.

The angle of the face and the shoulders changed according to the user's body conditions may cause cervical disk or obstruct sound sleep when the user lies on his or her side and sleeps while putting the side of his or her face on the side-of-face contact part 26.

In order to solve the above-mentioned problem, it is preferable to adjust the height of the pillow to maintain the right angle between the side of the face and the shoulders. For this, the slim pads 27 with thickness of 4.5 to 5.5 mm are provided to minutely adjust the angle between the side of the face and the shoulders.

Preferably, three to four slim pads 27 are stacked. Because the slim pads 27 are made of a foamed material, if the user uses without covering the pillow with a cover, central axes of the slim pads 27 may be dislocated when the user unconsciously pushes or pulls the slim pads 27 in sleep.

Therefore, in order to fix the positions of the slim pads 27 and maintain the fixed state, the cover body 28 having a friction increasing part 28a is combined with the outside of the slim pad 27.

The cover body 28 covers the outer surface of the slim pad 27, and is finished by thermosetting at the edge of the slim pad. In this instance, a plurality of the cover bodies 28 are stacked and the friction increasing parts 28a are interposed between the cover bodies 28 and between the surfaces of the side-of-face contact parts 26 to prevent the slim pads from being moved. The friction increasing parts 28a are made with any one among raised woven fabrics, such as suede fabric, velvet or lylex.

Here, not shown in the drawings, the fine height-adjusting part 29 may be disposed also at the lower portion of the cervical pillow 10. It is natural that the fine height-adjusting part 29 is applied to the cervical pillow 10 in the same way as the fine height-adjusting parts 29 disposed on the side pillows 20.

In this instance, the fine height-adjusting part 29 may be disposed on the side of the floor support part 40 mounted at the bottom of the cervical pillow 10, or may be disposed at the place of the floor support part 40, which is removed.

Therefore, the fine height-adjusting part 29 allows the user to lay with his or her head on the pillow in the most comfortable condition by adjusting the height of the side pillows 20 and the height of the cervical pillow 10.

Meanwhile, the wing parts 30 are connected to the bottom of the cervical pillow 10 and the bottoms of the side pillows 20 to prevent the cervical pillow 10 and the side pillows 20 from being moved.

The lower portion of the wing part 30 has the second and third or fourth sponges 22 formed at the lower portion, and the upper portion of the wing part 30 is made with a cloth, so that the wing part 30 protrudes inwards from the bottom surface toward the shoulder portions.

In general, people toss and turn several times in sleep, and in this instance, the pillow may be pushed out to wrong places.

Therefore, if the wing parts 30 are disposed inside the side pillows 20, preferably, in the recess parts 25 in which the shoulders are put, the shoulders are put on the wing parts 30 and the pillow is not separated due to a pressing action of the shoulders.

As described above, the cervical pillow 10, the side pillows 20, and the wing parts 30 which connect the cervical pillow 10 with the side pillows 20 are accommodated in the outer cover 60.

The outer cover 60 is made of a soft, flexible and air-permeable fabric material, and is cut and combined in the size and shape to prevent all of the components from being moved in the outer cover 60.

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear. In addition, a preferred embodiment of the present invention will be described hereinbelow, the technical thought of the present invention is not restricted or limited thereto and may be embodied in various manners through modification by those skilled in the art.

Figure 1:
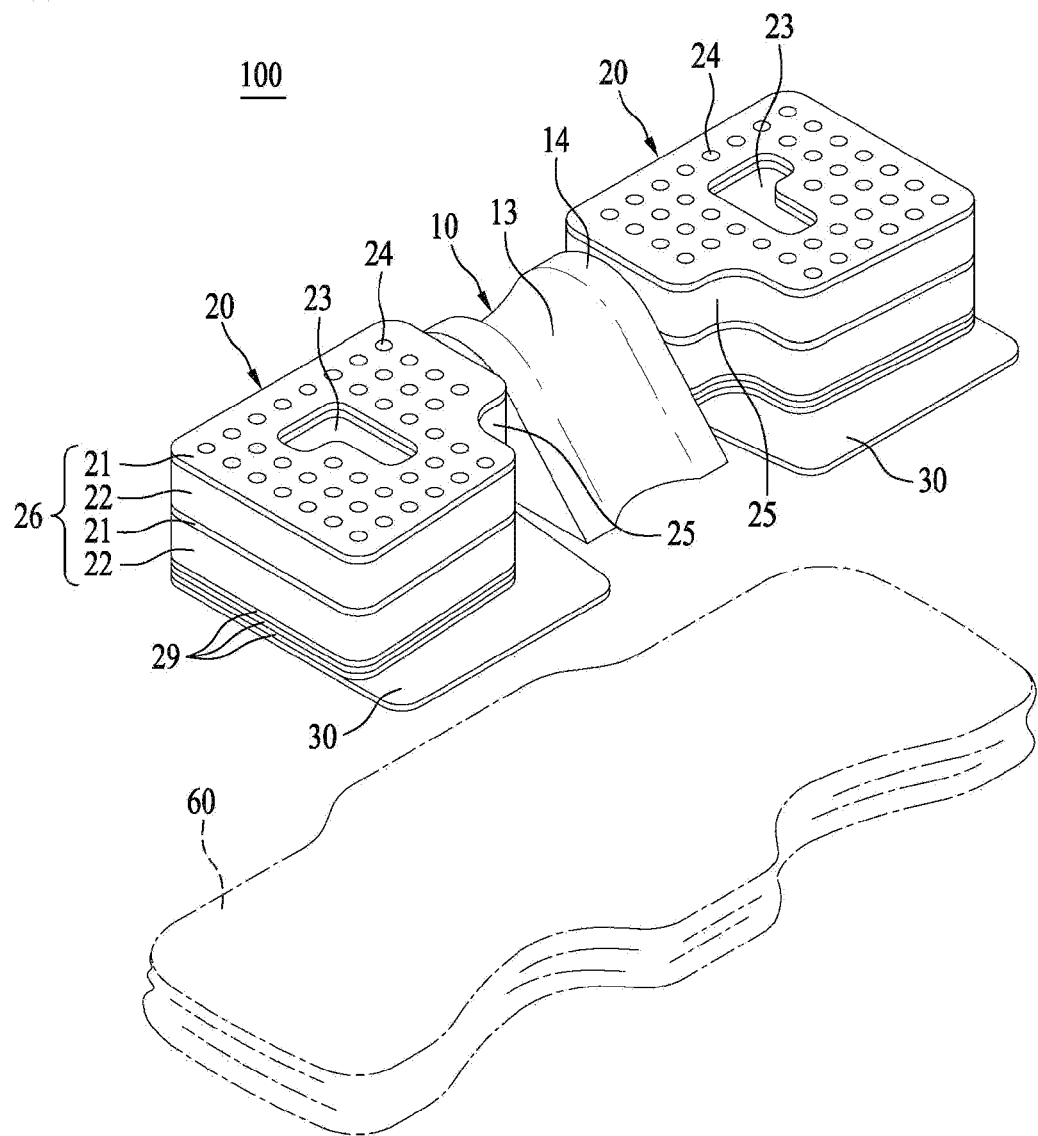
FIG. 1 is a perspective view showing a height-adjustable pillow according to a preferred embodiment of the present invention.
Figure 4A:
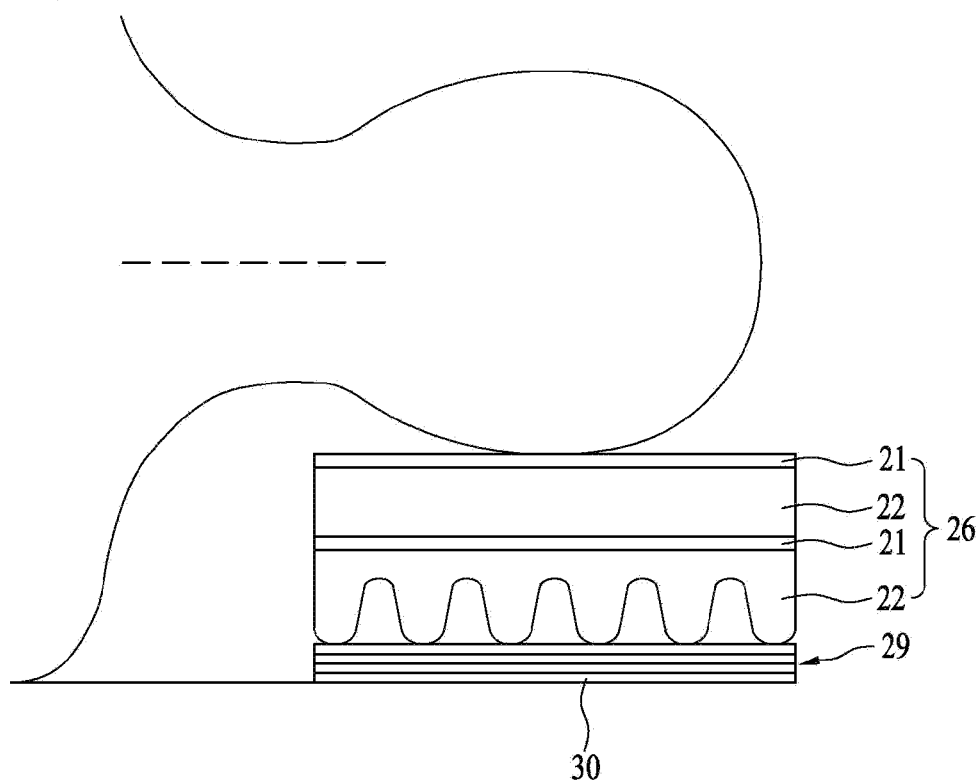
FIGS. 4a to 4c are perspective views showing only side pillows of the height-adjustable pillow according to the preferred embodiment of the present invention.
Figure 4B:
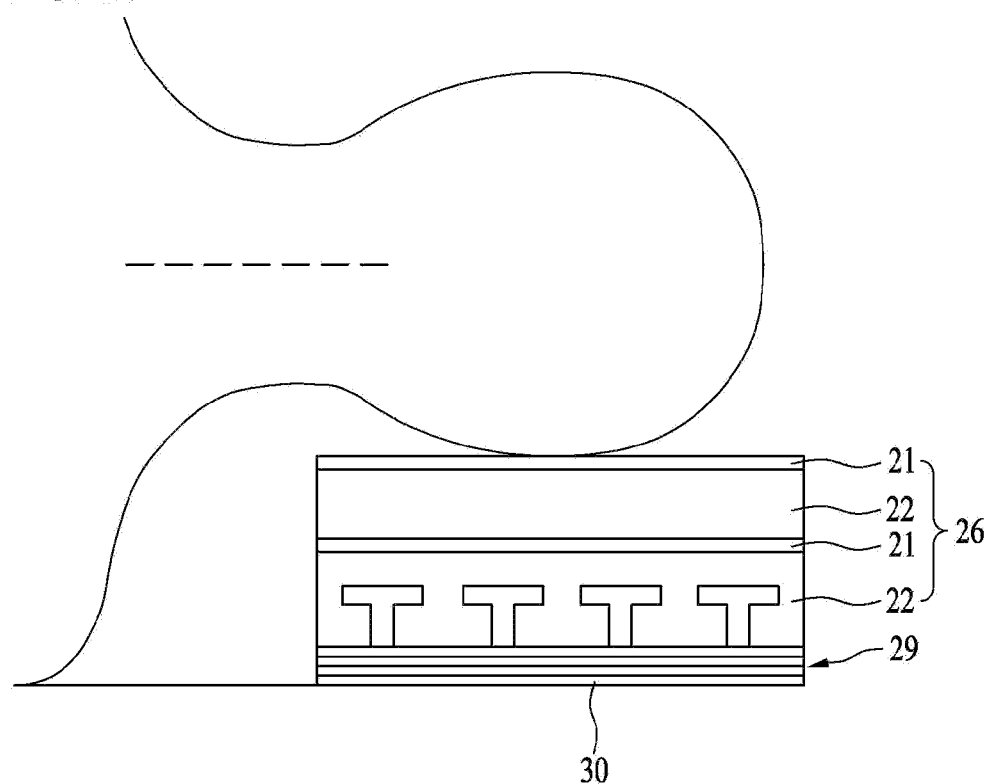
Figure 4C:
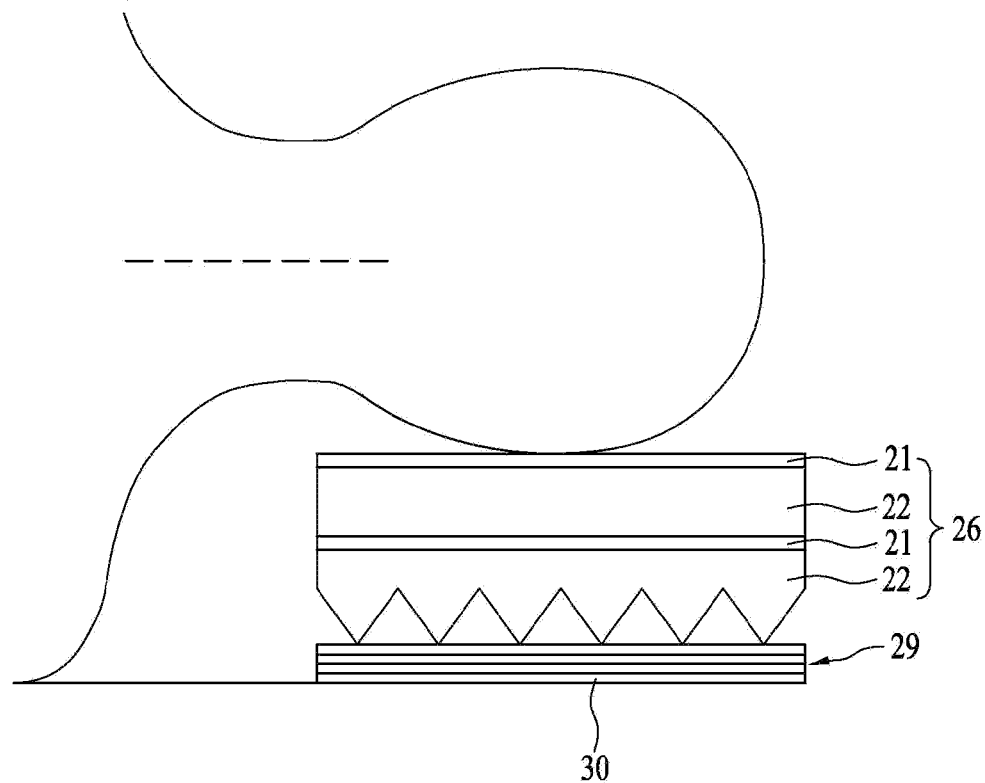
Figure 5:
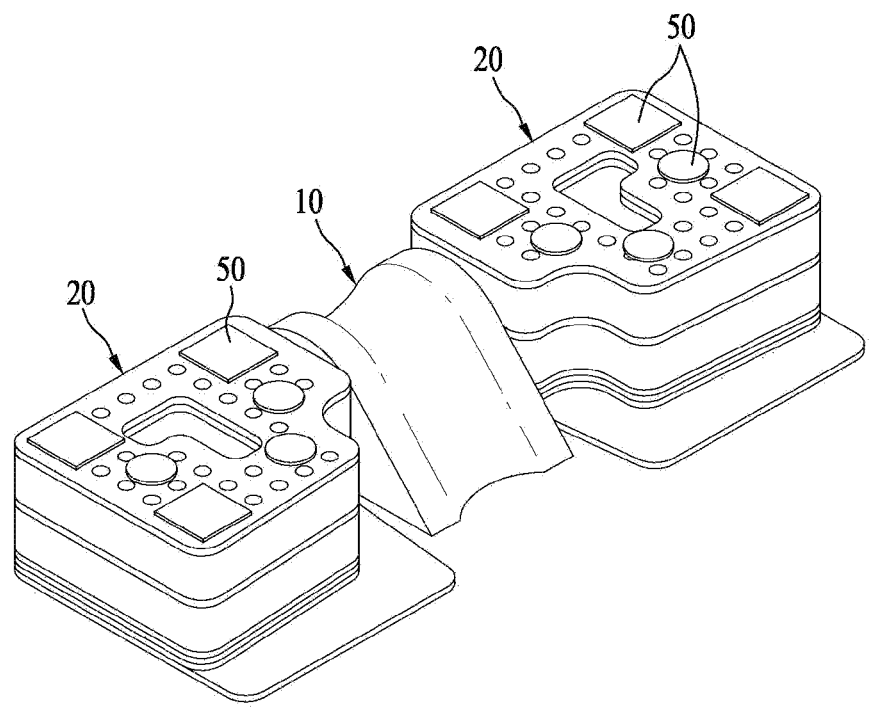
FIG. 5 is an exemplary view showing a state where cooling pads are disposed on the height-adjustable pillow according to the preferred embodiment of the present invention.
Figure 6:
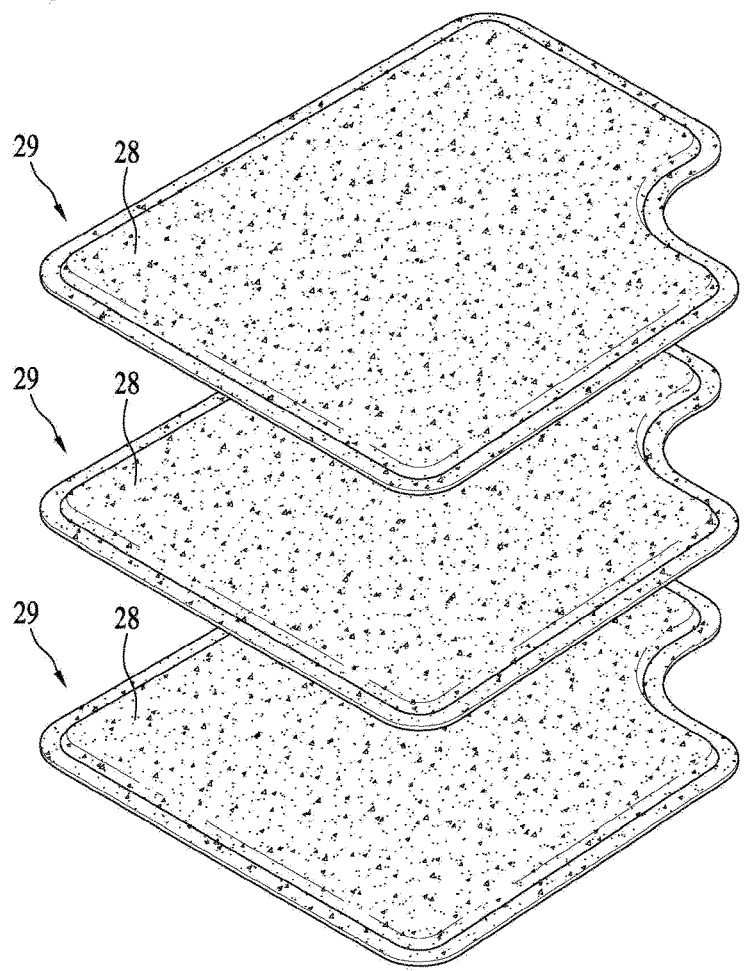
FIG. 6 is an exploded perspective view of the side pillow of the height-adjustable pillow according to the preferred embodiment of the present invention.
Figure 7:
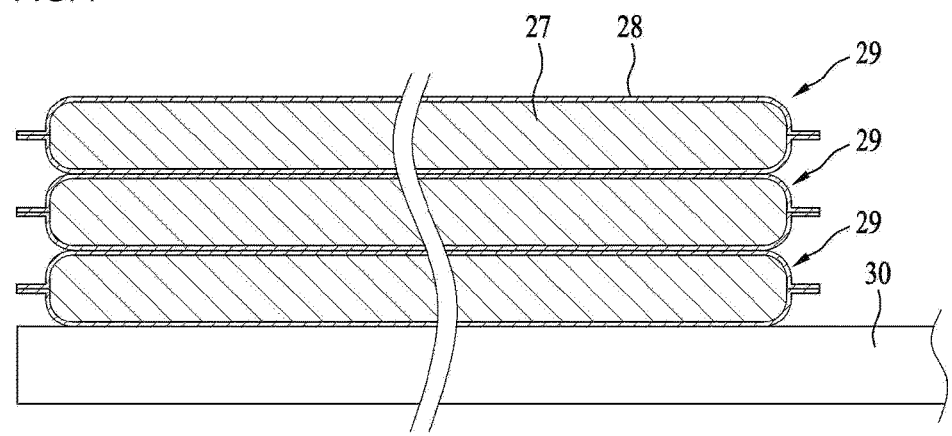
FIG. 7 is a sectional view showing that the side pillow of the height-adjustable pillow is cut.

FIG. 1 is a perspective view showing a height-adjustable pillow according to a preferred embodiment of the present invention, FIG. 2 is an exploded perspective view of a cervical pillow of the height-adjustable pillow according to the preferred embodiment of the present invention, FIG. 3 is a side sectional view showing a state where a floor support part disposed at the bottom of the cervical pillow of the height-adjustable pillow according to the preferred embodiment of the present invention, FIGS. 4a to 4c are perspective views showing only side pillows of the height-adjustable pillow according to the preferred embodiment of the present invention, FIG. 5 is an exemplary view showing a state where cooling pads are disposed on the height-adjustable pillow according to the preferred embodiment of the present invention, FIG. 6 is an exploded perspective view of the side pillow of the height-adjustable pillow according to the preferred embodiment of the present invention, FIG. 7 is a sectional view showing that the side pillow of the height-adjustable pillow is cut, and FIG. 8 is a partially enlarged view of a stacked portion of the side pillow of the height-adjustable pillow according to the preferred embodiment of the present invention.

Hereinafter, an action of the height-adjustable pillow according to the preferred embodiment of the present invention will be described.

In the state where the user rolls over on his or her side while getting the side of the face in close contact with the side-of-face contact part 26, if the neck portion and the shoulder portions do not keep at right angles and the head is raised or bent down so that the user feels inconvenient, the user removes the elastic pads from the side-of-face contact part 26, or removes the slim pad 27 from the fine height-adjusting part 29.

If the pillow needs a slight adjustment, the user removes the slim pads 27 stacked on the fine height-adjusting part 29 from the bottom one by one till obtaining the most comfortable condition.

In this instance, because the cover body 28 covering the outer surface of the slim pad 27 has the friction increasing part 28a, the user first removes the slim pad 27 and the cover body 28 which are arranged at the lowermost part and which have the friction increasing part 28a disposed only at the upper side thereof.

After that, if the shoulders of the user is widened through exercise or shoulder correction while using the pillow, the user puts the removed slim pad 27 between the stacked slim pads 27.

Here, because the cover body 28 having the fine height-adjusting part 29 is finished not by sewing but by thermal compression, the slim pads 27 can keep the firm state even though the user excessively pushes the head unconsciously in sleep. Especially, because the friction increasing part 28a disposed on the surface of the cover body 28 serves to hold the entire of the side pillows 20 to keep the stacked state so that the user can keep the neck healthy and the pillow can provide sufficient durability.

As described above, while the present invention has been particularly shown and described with reference to the example embodiments thereof, it will be understood by those of ordinary skill in the art that the above embodiments of the present invention are all exemplified and various changes, modifications and equivalents may be made therein without changing the essential characteristics and scope of the present invention. Therefore, it would be understood that the embodiments disclosed in the present invention are not to limit the technical idea of the present invention but to describe the present invention, and the technical and protective scope of the present invention shall be defined by the illustrated embodiments. It should be also understood that the protective scope of the present invention is interpreted by the following claims and all technical ideas within the equivalent scope belong to the technical scope of the present invention.

The invention claimed is:

1. A height-adjustable pillow comprising a cervical pillow including an outer shell and contents filled inside the outer shell so as to provide elasticity, wherein the outer shell and the contents have a loading part, which is recessed such that the cervical vertebrae and the occipital vertebrae are put thereon, and wall parts formed to protrude from both sides of the loading part; side pillows having a shape including side-of-face contact parts, which are attached to both sides of the cervical pillow and have a plurality of elastic pads formed in the same shape and stacked therein, and fine height-adjusting parts including a plurality of slim pads stacked at the lower portions of the side-of-face contact parts and cover bodies which encompass the outer surfaces of the plurality of slim pads and are formed by thermosetting to the edges thereof and which have friction increasing parts provided on the outer surfaces thereof; wing parts for connecting the lower portions of the cervical pillow and the side pillows; and an outer cover in which all constituent parts are accommodated and fitted.

2. The height-adjustable pillow according to claim 1, wherein the cervical pillow has a floor support part connected to the lower portion thereof.

3. The height-adjustable pillow according to claim 1, wherein the elastic pads and the slim pads have the same shape and form when viewed from the top.

4. The height-adjustable pillow according to claim 3, wherein the elastic pads and the slim pads are made of polyethylene foam, polyurethane foam, or EVA foam.

5. The height-adjustable pillow according to claim 1, wherein the side-of-face contact parts have ear seating parts and ventilation holes.

6. The height-adjustable pillow according to claim 1, wherein the side-of-face contact parts have first sponges of a filter foam material and second to fourth sponges of a highly elastic polyurethane foam material or a memory foam material, which are stacked alternately.

7. The height-adjustable pillow according to claim 1, wherein the cervical pillow and the side-of-face contact parts have cooling pads with a plurality of pieces of urethane gel stacked therein.

8. The height-adjustable pillow according to claim 1, wherein the cervical pillow has a plurality of acupressure protrusions formed to protrude.

* * * * *